Figure 2:
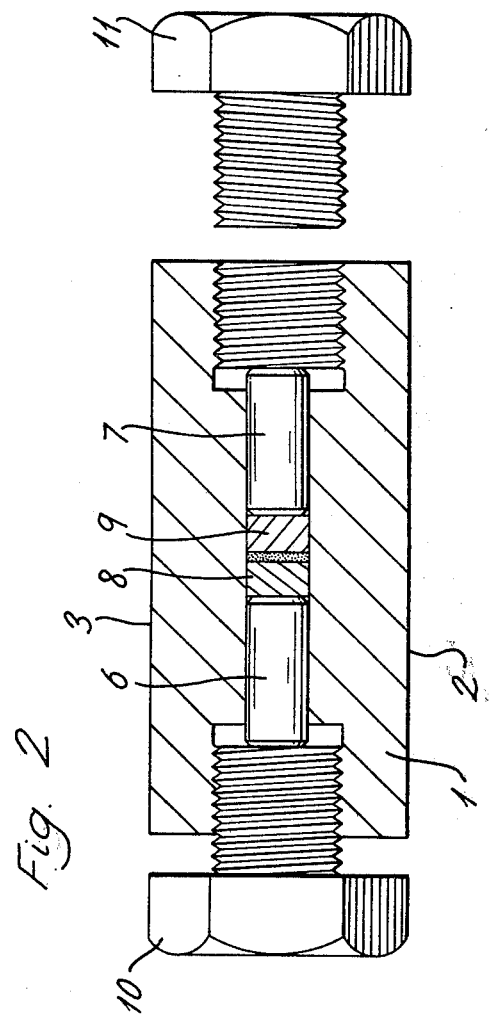

United States Patent [19]

Howe et al.

[11] 4,179,491
[45] Dec. 18, 1979

[54] ELECTRICAL DEVICE WITH SEPARATOR AS CONDUCTOR FOR HYDROGEN CATIONS

[75] Inventors: Arthur T. Howe; Mark G. Shilton, both of Leeds, England

[73] Assignee: National Research Development Corporation, London, England

[21] Appl. No.: 871,003

[22] Filed: Jan. 20, 1978

[30] Foreign Application Priority Data

Nov. 15, 1976 [GB] United Kingdom .............. 47470/76
May 5, 1977 [GB] United Kingdom .............. 18897/77

[51] Int. Cl.² ...................... C01G 43/00; H01M 8/10; H01M 6/18; G01N 27/46
[52] U.S. Cl. ...................................... 423/253; 429/33; 429/191; 204/242; 204/195 S; 204/1 T
[58] Field of Search ...................... 252/62.2, 301.1 R; 423/253; 429/33, 191; 204/1 H, 242, 195 S, 1 S; 350/160 R

[56] References Cited

U.S. PATENT DOCUMENTS 3,331,002  7/1967  Everitt ............................ 252/62.2 X
3,410,780  11/1968  Holden ............................ 204/195 S

*Primary Examiner*—John H. Mack
*Assistant Examiner*—D. R. Valentine
*Attorney, Agent, or Firm*—Cushman, Darby & Cushman

[57] ABSTRACT

The material $H(UO_2)XO_4 \cdot nH_2O$, where X is P, As or $I(OH)_2$, conducts protons and when pressed under steadily increasing pressure (subsequently gradually released) may find use as a component of a battery, fuel cell, electrochromic cell, water vapor pressure meter or the like.

3 Claims, 6 Drawing Figures

Fig. 1a
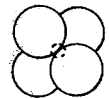
Fig. 1b
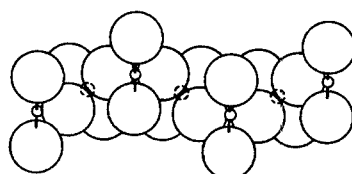
Fig. 1c
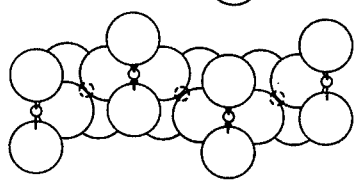
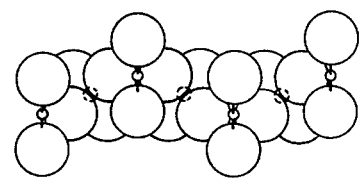
Fig. 1d
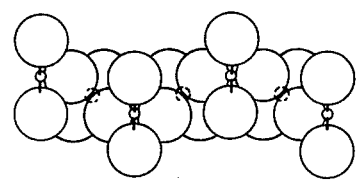

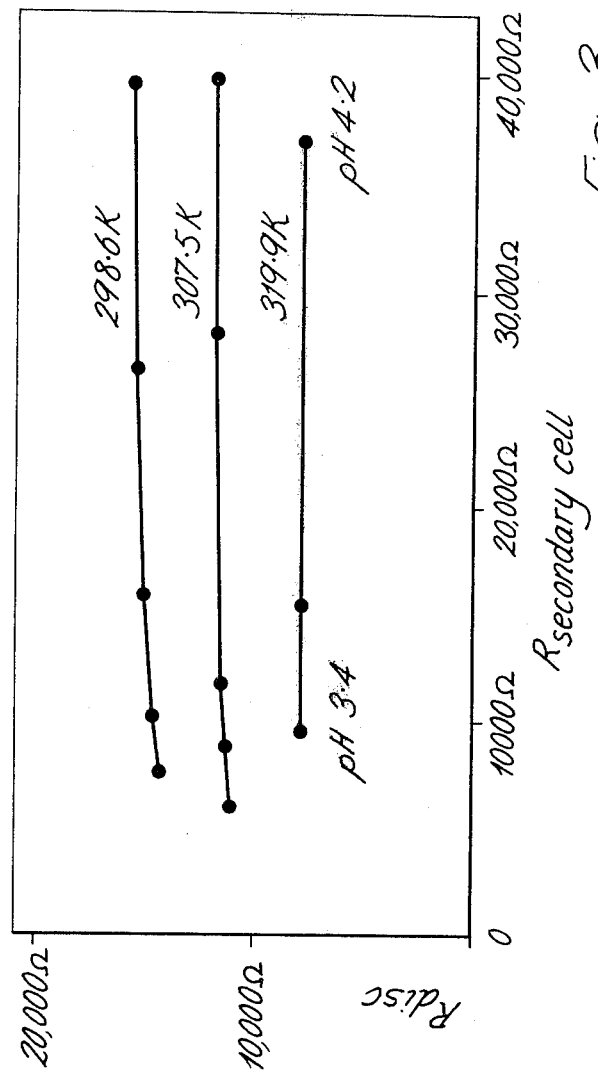

ELECTRICAL DEVICE WITH SEPARATOR AS CONDUCTOR FOR HYDROGEN CATIONS

This invention relates to an electrical device comprising a separator which is a conductor for hydrogen cations, and to a method of transmitting an electrical current in the form of hydrogen cations, using this separator.

An electrical device according to the invention thus comprises a separator which is a conductor for hydrogen cations, containing a single crystal or particles of one or more of the compounds (i) $H(UO_2)PO_4.nH_2O$
(ii) $H(UO_2)AsO_4.nH_2O$
(iii) $H(UO_2)IO_4(OH)_2. nH_2O$ wherein a proportion of the H, preferably not more than 50% by charge, may be replaced by one or more other cations, for example $Li^+$, $Na^+$, $K^+$, $NH_4^+$, $Cu^{++}$, $Mg^{++}$, $Ca^{++}$, $Ba^{++}$, $Sr^{++}$, $Pb^{++}$, $Fe^{++}$, $Co^{++}$, $Ni^{++}$, $Mn^{++}$, or $Al^{+++}$; as long as the conductivity is acceptable for operation of the device.

The conductor may be physical mixtures of the above, or may contain mixtures of appropriate components as solid solution, for example a mixed phosphate-arsenate.

The above compounds have molecules of crystallisation preferably all water, some of which may be replaced by neutral molecules such as alcohols, amines or organic molecules having two donor groups or mixtures of these. The number and type of molecules of crystallisation are variable as long as the conductivity is acceptable for operation of the device. The number (n) of molecules of crystallisation in the case of water is typically approximately 4 but other values, for example in the vicinity of 5, may occur, depending on the preparation conditions. Compounds wherein $H^+$ has been partially substituted by metal ion may have more or fewer waters of crystallisation. For good conductivity, n preferably exceeds 2.

Impurities which do not destroy the conductivity of the particles can be tolerated. The $UO_2:PO_4$ or $UO_2:AsO_4$ or $UO_2:IO_4$ molar ratio may be up to 10% either way of unity.

The electrical device may be for example an electrolysis cell, a water vapour pressure meter, an electrochromic cell, a battery, a hydrogen purifier, a hydrogen-isotope enricher, a proton-sensitive electrode (e.g. for a pH meter) or a fuel cell, in which the fuel may be hydrogen.

Generally, in such a fuel cell, the hydrogen, usually in the form of a gas, passes an electrode which strips the electrons from the gas; the resulting hydrogen cations travel through the separator, which contacts the electrode, until they reach another electrode. Meanwhile the electrons stripped from the hydrogen can do useful electrical work in a circuit which leads to this other electrode. Here, the electrons are accepted by oxygen to form 0 in the −2 oxidation state, which combines with the hydrogen cations to form water, releasing energy which is the driving force for the other steps described.

The battery may for example use a solid-state system such as $Cu|PdH_x|separator|ZrH_y|Cu$ or other systems whose driving force is the difference in stability between different metal hydrides; in the above example the following reaction releases energy: $PdH_x + ZrH_y \rightarrow PdH_{x-\sigma} + ZrH_{y+\sigma}$. Here, the Pd could be replaced by the cheaper alloy $LaNi_5$ or $TiFe_2$, or for example the battery could be $CaH_x|separator|TiFeH_{2-x}$, and may be potted in epoxy resin for rigidity and to avoid gas losses, and may be assembled in a discharged, part-charged or fully charged form, as convenient. Alternatively, oxygen or air could be used instead of the metal hydride having the lower hydrogen vapour pressure. In such a case, the battery would be a primary (irreversible) battery of the form $CaH_2|separator|air$. At the air electrode, hydrogen is oxidised to form, as a waste product, water, which evaporates away. Instead of calcium hydride, the already mentioned hydrides of zirconium, palladium, $LaNi_5$ or TiFe, or other (e.g. alkaline earth) hydrides may be tried.

The water vapour pressure meter operates having two half-cells each of which is based on the reaction $O_2 + 4e 4H^+ 2H_2O$. In one half-cell the vapour pressure of water is set at a reference level and, from the output voltage, the water vapour pressure in the other half-cell may be determined.

Another application is for an hydrogen isotope enricher. Differences in the diffusion rate of the hydrogen isotopes $H^1$, $H^2$ (deuterium) and $H^3$ (tritium) may be utilised to enable an enrichment. Consider the following system

| acid | separator | acid |
| Pd | | Pd |

When a small potential is applied across the Pd electrodes a hydrogen ion current will flow which will result in more of the faster moving isotopes being transferred from one side to the other side of the compact. The longer the time of current passage the greater the enrichment of the supply compartment, to which replacement water may need to be added during the operation.

In an electrochromic cell, $H_xMoO_3$ or $H_xWO_3$ or a similar coloured hydride may form one electrode in contact, through a separator as defined above, with a counterelectrode which be the same or a different hydride or a metal such as gold.

The invention also provides a method of transmitting an electric current in the form of hydrogen cations, wherein the conductor for the hydrogen cations is a separator as defined above.

Separators, especially of compound (i) and/or (ii), may be formed by applying pressure to a mass of particles of the compound. The density, hardness, and solubility requirements of any particular compact pressed from any particular compound will be determined by the type of device in which it is to be used. Examples will be given later. Preferably pressing is done starting with particles moistened with water or suitable acid so as to form a still paste initially. Preferably the pressure is maintained for several days. Pressures steadily increased up to approximately 2 tonnes per square cm can be used and before removing the separator should be gradually reduced to zero, otherwise the separator may crack.

Separators can be made in the form of films by spreading a slurry of freshly prepared and unwashed precipitate over an area and allowing the slurry to evaporate slowly in air over a period of preferably 1 day. Films which are coherent, and in which the particles are not loose, can be made in this way. Such films may be more convenient than discs in electrochromic cells or solid-state batteries, and have the advantage of thinness and in addition the orientation of the particles will be more random than in a pressed disc, thus enhancing the conductivity in the transverse direction.

Separators can also be made by suspending particles of the compound in a woven material.

Part of the conductivity of the separator may arise because of the presence of acid as solution between the particles. The conductivities of many of the separators can be substantially increased by soaking in acid. The separator will suffer a deterioration in hydrogen ion conductivity if heated excessively.

The invention will now be described by way of example with reference to the accompanying drawings.

In FIG. 1, the structures of some uranyl phosphates are schematically illustrated.

FIGS. 2 and 3 show, respectively, a fabricating apparatus and a conductivity graph, and are described later.

EXAMPLE 1

HYDROGEN URANYL PHOSPHATE HYDRATE

Consideration of the structure of hydrogen uranyl phosphate, $H(UO_2)PO_4 \cdot nH_2O$, shows that each uranyl cation $UO_2^{2+}$ is linear with O—U—O structure as shown in FIG. 1a, and is co-ordinated to four oxygen ions each from a separate phosphate group, in such a way that each U(VI) atom has co-ordination to six oxygen atoms. Each phosphate ion $PO_4^{3-}$ (as shown in FIG. 1b) is approximately tetrahedral as regards the oxygen atoms, each of which is co-ordinated to a separate uranyl ion. In this way there is formed an indefinitely extending two-dimensional layer represented as $(UO_2PO_4)_q{}^{q-}$, with the uranyl ions standing perpendicularly to the layer, as seen in FIG. 1c. If the $UO_2^{2+}$ ion were not linear, such a regular arrangement would not be possible. The layers are stacked directly above each other ("AAA ..."), FIG. 1c. In some cases, where M is principally certain divalent cations, the layers are stacked in an ABAB ... arrangement, as seen in FIG. 1d. In both cases, cations M and water molecules $nH_2O$ occupy interstices between the layers, forming a connected sheet.

The structure of FIG. 1c is a meta-autunite or meta-torbernite. The structure of FIG. 1d is autunite or torbernite and in this case a way of considering the relationship between A layers and B layers is to regard B as the mirror image of A given a mirror plane parallel to A.

SYNTHESIS OF HYDROGEN URANYL PHOSPHATE

A concentrated solution of uranyl nitrate $UO_2(NO_3)_2$ in water was made up, and added in equimolar proportions to a 2.3 M aqueous solution of phosphoric acid $H_3PO_4$. The mixture was continuously stirred for a period of 24 hours at 0° C. (although from 1 hour upwards may be suitable, and from 0° C. to 30° C. may be suitable). During this time fine pale-yellow flat plate-like crystals of hydrogen uranyl phosphate $HUO_2PO_4 \cdot nH_2O$ were precipitated. Accompanying the precipitation, of course, nitric acid was liberated. The precipitate, if to be pressed, is treated as described in the next section.

The precipitate (if to be stored) was filtered and washed with small volumes of water until the wash liquid was pH 2. The precipitate could be stored in solution, or could be dried out in the atmosphere, where, at ambient temperature and normal water vapour pressure, it was stable.

Thermal gravimetric analysis showed that each mole of $HUO_2PO_4 \cdot nH_2O$ had approximately 4 moles of water of crystallisation at room temperature.

The rather slow rate of precipitation could be enhanced both by using dilute solutions and by increasing the temperature but the precipitate so obtained was less suitable for the disc fabrication step, to be described.

X-ray diffraction studies showed the compound to be highly crystalline with an exaggerated (001) intensity, that is, a partial orientation of the flat crystals.

The possibility of ions being taken up into the layers, in equal equivalents of cations and anions, cannot be ruled out.

FABRICATION OF DISCS

One satisfactory way of fabricating separators in the form of discs of powdered hydrated hydrogen uranyl phosphate is to allow a quantity of the powder to settle from solution. The powder is filtered without washing and is then placed in a disc press suitable for compressing infra-red quality KBr, slowly increasing the pressure to 2 tonnes per square cm.

Under optimum conditions tinted transparent discs of density greater than 99% of theoretical could be obtained which were robust, and slightly brittle, and withstood being dropped on the floor from 1 m.

In order to determine when the pressing had produced a transparent disc it was found convenient to use a transparent plastics die, with stainless steel plungers. Pressing was continued until the whole thickness of the disc appeared translucent, which typically took several days, depending on the thickness. The pressing time was minimised by using the precipitate fresh after preparation. If left in solution it was found that the particle size gradually increased, which is disadvantageous to pressing. It was also found beneficial not to wash the precipitate before pressing, but to load the slurry from the preparation, after filtering, directly into the press. A preferred method of fabricating the separator therefore comprises pressing a sample of precipitated compound in contact and in equilibrium with supernatant liquor from which it has been precipitated.

The actual pressure applied to compress the disc appeared to be less important than the duration and rate of increase of the pressure; pressures over 1 tonne per square cm, preferably over 2 tonnes per square cm, could be used.

Shorter pressing times produced opaque discs which were nevertheless quite robust. For robust discs the duration of pressure was preferably at least 3 hours, or for robust translucent discs preferably at least 20 hours, more preferably at least 72 hours. Periods of less than a few minutes rarely gave satisfactory results.

It was preferable to increase the pressure to its maximum in small stages or continuously, so as to avoid extruding particles out of the die. After the allotted pressing time, pressure was reduced steadily to zero over a period of 2 hours.

Those discs, fabricated as above, which were selected for use, were translucent and within 99% of the theroretical density, indicating that there were negligible cracks and voids in the disc and that true sintering had occurred. The translucency showed that the grain boundary regions must be smaller than the wavelength of visible radiation. X-ray analysis of discs showed a preferred orientation of the crystals parallel to the disc face, more so than in the normal powder. Orientation however was not complete since (001) reflections were clearly visible in the other directions, though markedly reduced in intensity. Thermal gravimetric analysis showed that discs (like the powder) had approximately 4 moles of water of crystalization per mole of hydrogen uranyl phosphate, showing that pressing does not squeeze water out of the structure.

The discs retained their properties even after months in air. In phosphoric acid solution of pH 2.4 the discs remained transluscent for extended periods of time, typically many days or longer depending on the initial quality of the disc. Thermodynamically, at pH exceeding about 2.6, hydrogen uranyl phosphate is less stable than triuranyl diphosphate, but transformation is kinetically slow in non-alkaline conditions. In water, or dilute salt solutions, no substantial swelling was observed, but a cloudiness slowly formed on the surfaces of the disc. When the pH was below 2, the disc dissolved more quickly; for example, the dissolution rate with stirring at room temperature at pH 0.8 was found to be of the order of 0.1 mm per day. Suitable amounts of phosphate ion and uranyl ion added to the solvent inhibited dissolution.

A disc was tested for permeability to gaseous hydrogen. There was no detectable passage of hydrogen after 70 hours at an overpressure of 100 torr.

Discs could also be pressed at elevated temperatures. Good quality hydrogen uranyl phosphate discs could be pressed at 80° C. The technique is particularly suitable for the pressing of the metal substituted uranyl phosphates, which are even more insoluble than hydrogen uranyl phosphate. For these the sintering process appears to be slower, taking up to 14 days. However robust semi-translucent discs of lithium uranyl phosphate could be pressed at 80° C., of which part of the lithium could be subsequently exchanged for hydrogen in acid solutions so as to produce a separator according to the invention.

For convenience in pressing at high temperatures the apparatus shown in FIG. 2 of the accompanying drawings was used for preference. A cylindrical body 1 has external flats 2 and 3 to enable the body 1 to be held fast against rotation, in a vice. The body 1 has an axial passage some 10 mm in diameter containing slidable plungers 6,7 and slidable dies 8,9. Both ends of the axial passage are enlarged and screw-threaded. However, the screw threads at each end are of opposite hand. Bolts 10,11 are compatible with these threads.

In use, the body 1 is held in a vice immersible in a heated water bath. A sample to be compressed (enough to give a finished thickness of 1 mm for example) is placed in the axial passage of the body between the dies 8 and 9, and the plungers 6 and 7 are put in place. The bolts 10 and 11 are screwed in, and box spanners (not shown) are applied to the bolts. The shanks of the spanners are fastened together by a cross-piece from which a weight is hung such as to tighten the bolts. From the size of the weight, the pressure exerted by the dies 8 and 9 can be calculated. This method of tightening the bolts, ie. rotating them in the same absolute sense, makes for simpler control and ensures that the sample to be compressed is not subjected to torque. It also simplifies the advisable slow reduction of pressure before removal of the sample.

DEMONSTRATION OF DISC CONDUCTIVITY

A solution electrochemical cell was set up as follows. A vessel was divided into two compartments by a watertight partition. The partition then had a hole drilled in it, and the hole was plugged by a disc fabricated as above. The disc was set standing up perpendicular to the partition, so that the preferred orientation of the $UO_2PO_4^-$ layers (and consequently of the $H^+nH_2O$ sheets) was also perpendicular to the partition. The disc was secured with epoxy resin to ensure that the partition was again watertight.

The disc of hydrogen uranyl phosphate thus formed a separator between the two compartments able to conduct hydrogen cations. The compartments were filled with various solutions arranged to be stirred and also subject to temperature control to within 0.1+ C. One palladium black electrode was pressed up against each side of the disc. Meanwhile, a secondary cell consisting of two platinum black plates was dipped into one of the two solutions; in this way the conductivities of the solutions alone could be readily simultaneously measured.

For measuring a.c. conductivity, a Wayne-Kerr variable cpacity bridge was used to provide a frequency of 1592 kHz. For both sets of electrodes, the conductivity only changed by about 5% on changing the frequency from 0.1 to 15 kHz, showing that polarisation effects were very small. While measuring d.c. conductivity, the current was intentionally limited so that polarisation effects were not appreciable. Keighley digital voltmeters of $10^7$ ohm impedance were used. The results obtained with a.c. seemed more accurate, and have been relied upon.

The cell was operated under a.c. voltage with solutions of phosphoric acid or concentrations arranged to give various values of pH from 1.5 to 6. From pH6 down to pH2, the solution conductivity was less than that of the disc, and any layer of solution between the disc surfaces and the electrodes contributed significantly to the total cell resistance. However, from pH2 down to 1.5, the cell resistivity depended much less on any solution effects. Measurements at pH 0.8 were restricted to a duration of one week, owing to dissolution of the disc.

Direct resistivity measurements on a disc in air gave a similar result.

There was some drift of cell resistance following a change in pH. The cell resistance would change to a new value almost instantly, but this value would then drift up to 5%, becoming steady within half to 1 hour. This shows a satisfactorily small degree of solution uptake between or within the grains of the hydrogen uranyl phosphate. Poorly pressed discs, which incidentally were opaque, showed bad resistivity value drifting, as would be expected from the above.

In FIG. 3 of the accompanying drawings, $R_{disc}$ (in ohms) is plotted against $R_{secondary\ cell}$. The disc is the hydrogen uranyl phosphate disc just described, and separates two solutions of dilute phosphoric acid each of which contains an electrode. The solutions, the disc and the electrodes thus constitute the cell. The pH of the solutions (which were kept identical to each other) was changed over the range 3.4 to 4.2. FIG. 3 shows, from the extreme shallowness of the gradients, that the disc resistance is virtually unaffected by the pH of the surrounding solutions. Thus, the disc may be taken to be essentially impermeable to the solutions, and the resistance measured as $R_{disc}$ may be taken truly to represent the resistivity of the disc. Measurements for the graphs of FIG. 3 were nonetheless only taken after an equilibration period, to allow for any possible solution uptake by the disc.

In the above cases, absolute values of the conductivity could not be calculated because the electrodes were small compared with the disc surface. However, similar measurements using large electrodes pressed onto the disc arranged with the conducting path between them parallel to the flat faces gave a value of the conductivity at 300° K. of about $4 \times 10^{-3}$ ohm$^{-1}$cm$^{-1}$.

Discs mounted so as to conduct perpendicularly to the preferred direction of $UO_2PO_4^-$ layers showed a conductivity which was poorer by a factor typically of only 4 to 10. The anisotropy varied with the degree of pressing of the disc.

Conductivity measurements carried out at 100° C. in steam showed the conductivity perpendicular to the preferred layer direction to be reasonable.

EXAMPLE 2

HYDROGEN URANYL ARSENATE

Hydrogen uranyl arsenate, $H(UO_2)AsO_4.nH_2O$, is substantially isostructural with hydrogen uranyl phosphate, and therefore the discussion of the structure of the latter in Example 1 applies equally to this compound. Hydrogen uranyl arsenate can be prepared under similar conditions to hydrogen uranyl phosphate. For example the following is suitable. A concentrated solution of uranyl nitrate $UO_2(NO_3)_2$ in water was made up, and added in equimolar proportions to a 2.8 M aqueous solution of arsenic acid $H_3AsO_4$. The mixture was stirred continuously for 24 hours at 0° C. and during this time the precipitate of hydrogen uranyl arsenate formed, but the conditions could be varied as in Example 1.

Translucent discs could be pressed at room temperature generally as described in Example 1. The conductivity of the discs parallel to the faces was typically approximately $10^{-3}$ ohm$^{-1}$cm$^{-1}$ at room temperature.

EXAMPLE 3

HYDROGEN URANYL PERIODATE

Hydrogen uranyl periodate, $H(UO_2)IO_4(OH)_2nH_2O$, may be synthesised for example by adding periodic acid solution to a uranyl solution, preferably uranyl acetate, or to uranyl hydroxide, such that the total ratio of uranyl to periodate is preferably in the region of 1:1. The initial precipitate is sometimes $H(UO_2)_2IO_6.pH_2O$ or the like, and should be left as the solutions are allowed to evaporate, when the desired $H(UO_2)IO_4(OH)_2.nH_2O$ is finally produced.

In the case of uranyl acetate, acetic acid, which is volatile, is lost upon evaporation to leave the desired compound. In the case of uranyl hydroxide, no unwanted ions require to be removed.

An alternative notation for the desired compound $H(UO_2)IO_4(OH)_2nH_2O$ is $H_3(UO_2)IO_6.nH_2O$. The structure is uncertain.

We claim:

1. An electrical device including a separator which is a conductor for hydrogen cations, said conductor comprising the material

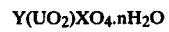

$Y(UO_2)XO_4.nH_2O$ wherein Y is a cation which is at least partially H cation, the remainder being at least one other cation, and wherein X is phosphorous, arsenic or $I(OH)_2$ and wherein n is at about its equilibrium value, said device further including means for causing said hydrogen cations to pass through said separator.

2. The article of claim 1, wherein a proportion of the Y is substituted by at least one other cation.

3. The article of claim 2, wherein up to 50% by charge of the Y is substituted by at least one other cation.

* * * * *

UNITED STATES PATENT AND TRADEMARK OFFICE
CERTIFICATE OF CORRECTION

PATENT NO. : 4,179,491

DATED : December 18, 1979

INVENTOR(S) : Arthur T. Howe and Mark G. Shilton

It is certified that error appears in the above—identified patent and that said Letters Patent is hereby corrected as shown below:

In foreign application priority data delete

--Nov. 15, 1976 [GB] United Kingdom 47470/76 --

Signed and Sealed this

Sixth Day of May 1980

[SEAL]

Attest:

SIDNEY A. DIAMOND

Attesting Officer

Commissioner of Patents and Trademarks